(12) United States Patent
Butler

(10) Patent No.: US 9,375,706 B2
(45) Date of Patent: Jun. 28, 2016

(54) USE OF SWING PRELIMINARY ALKYLATION REACTORS

(75) Inventor: James Butler, League City, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 135 days.

(21) Appl. No.: 13/028,381

(22) Filed: Feb. 16, 2011

(65) Prior Publication Data

US 2011/0184218 A1 Jul. 28, 2011

Related U.S. Application Data

(63) Continuation-in-part of application No. 11/515,679, filed on Sep. 5, 2006, now abandoned.

(51) Int. Cl.
*B01J 29/04* (2006.01)
*B01J 29/06* (2006.01)
(Continued)

(52) U.S. Cl.
CPC .............. *B01J 29/06* (2013.01); *B01J 29/7057* (2013.01); *B01J 29/90* (2013.01); *C07C 2/66* (2013.01);
(Continued)

(58) Field of Classification Search
CPC ................ B01J 19/00; B01J 8/00; B01J 7/00; B01J 19/1862; B01J 2219/00–2219/00006; B01J 14/00; B01J 19/24; B01J 29/04; B01J 29/06; B01J 29/70; B01J 29/7049; B01J 29/7057; B01J 29/90; A01N 59/00; B82Y 40/00; C07C 15/08; C07C 29/1518; C07C 31/08; C07C 209/48; C07C 2/66; C07C 4/06; C07C 11/04; C07C 11/06; C07C 2/54; C07C 2/64; C07C 6/08; C07C 6/12; C07C 6/126; C07C 7/12; C07C 15/02; C07C 15/067; C07C 15/073; C07C 2529/04; C07C 2529/06; C07C 2529/08; C07C 2529/70; B01D 3/009
USPC .......... 422/129, 600, 630, 631, 187; 588/310, 588/319, 323, 400, 446, 448, 449; 585/310, 585/319, 323, 400, 446, 448, 449
See application file for complete search history.

(56) References Cited

U.S. PATENT DOCUMENTS 3,308,069 A 3/1967 Wadlinger et al.
4,185,040 A 1/1980 Ward et al.
(Continued)

FOREIGN PATENT DOCUMENTS

CN 1764620 A * 4/2006
EP 0776876 B1 * 6/2000 ................ C07C 2/66
(Continued)

OTHER PUBLICATIONS

Chinese Office Action issued in Chinese Application No. 201110046385.1 mailed on Mar. 15, 2013, and English translation thereof (17 pages).
(Continued)

*Primary Examiner* — Natasha Young
(74) *Attorney, Agent, or Firm* — Albert Shung

(57) ABSTRACT

Alkylation systems and processes are described herein. The alkylation system generally includes a preliminary alkylation system containing a preliminary alkylation catalyst therein and adapted to contact an aromatic compound and an alkylating agent with the preliminary alkylation catalyst so as to alkylate the aromatic compound and form a preliminary output stream, wherein the preliminary alkylation system includes a first preliminary alkylation reactor and a second preliminary alkylation reactor connected in parallel to the first preliminary alkylation reactor and a primary alkylation system adapted to receive the preliminary output stream and contact the preliminary output stream and the alkylating agent with a primary alkylation catalyst disposed therein so as to form a primary output stream.

14 Claims, 2 Drawing Sheets

(51) Int. Cl.

| | | |
|---|---|---|
| *B01J 29/70* | (2006.01) | |
| *B01J 29/90* | (2006.01) | |
| *C07C 2/54* | (2006.01) | |
| *C07C 2/64* | (2006.01) | |
| *C07C 2/66* | (2006.01) | |
| *C07C 6/08* | (2006.01) | |
| *C07C 6/12* | (2006.01) | |
| *C07C 7/12* | (2006.01) | |
| *C07C 15/073* | (2006.01) | |
| *B01J 19/00* | (2006.01) | |
| *B01J 19/24* | (2006.01) | |
| *C07C 15/02* | (2006.01) | |
| *C07C 15/067* | (2006.01) | |

(52) U.S. Cl.
CPC . *C07C 6/126* (2013.01); *C07C 7/12* (2013.01); *C07C 15/073* (2013.01); *B01J 2219/00006* (2013.01); *C07C 2529/08* (2013.01); *C07C 2529/70* (2013.01); *Y02P 20/52* (2015.11); *Y02P 20/584* (2015.11)

(56) References Cited

U.S. PATENT DOCUMENTS

| | | | |
|---|---|---|---|
| 4,358,362 A | 11/1982 | Smith et al. | |
| 4,642,226 A | 2/1987 | Calvert et al. | |
| 4,992,606 A | 2/1991 | Kushnerick et al. | |
| 5,081,323 A | 1/1992 | Innes et al. | |
| 5,258,565 A | 11/1993 | Kresge et al. | |
| 5,453,554 A | 9/1995 | Cheng et al. | |
| 5,535,817 A | 7/1996 | Dunne | |
| 6,002,057 A | 12/1999 | Hendriksen et al. | |
| 6,057,485 A | 5/2000 | Merrill et al. | |
| 6,297,417 B1 | 10/2001 | Samson et al. | |
| 6,376,729 B1 * | 4/2002 | Merrill et al. | 585/449 |
| 6,617,482 B1 | 9/2003 | Venkat et al. | |
| 7,645,913 B2 | 1/2010 | Clark et al. | |
| 7,777,087 B2 | 8/2010 | Clark et al. | |
| 2003/0149324 A1 | 8/2003 | Venkat et al. | |
| 2004/0068151 A1 | 4/2004 | Kelly et al. | |
| 2004/0192985 A1 | 9/2004 | Smith | |
| 2005/0075237 A1 * | 4/2005 | Kelly et al. | 502/49 |
| 2005/0143612 A1 | 6/2005 | Hwang et al. | |
| 2006/0192985 A1 | 8/2006 | Butler | |
| 2010/0268008 A1 | 10/2010 | Hwang et al. | |

FOREIGN PATENT DOCUMENTS

| | | |
|---|---|---|
| WO | 9429245 A1 | 12/1994 |
| WO | WO 02/14240 A1 * | 2/2002 |
| WO | 2004085352 A2 | 10/2004 |

OTHER PUBLICATIONS

Xie Zaiku et al., "Effect of Treatment with NaAlO2 Solution on the Surface Acid Properties of Zeolite β"; J. Catel. 205, 58-66 (2002).

* cited by examiner

USE OF SWING PRELIMINARY ALKYLATION REACTORS

CROSS-REFERENCE TO RELATED APPLICATIONS

This application claims the benefit of U.S. patent application Ser. No. 11/515,679, filed Sep. 5, 2006.

FIELD

Embodiments of the disclosed invention generally relate to alkylation of aromatic compounds. In particular, embodiments of the invention generally relate to regeneration of alkylation catalyst used in the alkylation of aromatic compounds.

BACKGROUND

Vinyl aromatic compounds, such as styrene, are used in the manufacture of many polymers. Styrene can be produced in a dehydrogenation process by contacting ethylbenzene and steam with a dehydrogenation catalyst, and ethylbenzene can be formed in an alkylation process by contacting benzene and an alkene with an alkylation catalyst. The dehydrogenation process can be used in conjunction with the alkylation process, where the product stream of ethylbenzene from the alkylation process is used as the input stream for the dehydrogenation process, for example.

Alkylation systems require periodic maintenance, which can include regeneration or replacement of the catalyst utilized in various portions of the alkylation system. Such maintenance causes system disruption and often system shutdown. Therefore, it is desirable to develop processes and systems capable of lengthening periods between maintenance and potentially avoiding system shutdown.

SUMMARY

One or more embodiments include an alkylation system. The alkylation system generally includes a preliminary alkylation system containing a preliminary alkylation catalyst therein and adapted to contact an aromatic compound and an alkylating agent with the preliminary alkylation catalyst so as to alkylate the aromatic compound and form a preliminary output stream, wherein the preliminary alkylation system includes a first preliminary alkylation reactor and a second preliminary alkylation reactor connected in parallel to the first preliminary alkylation reactor and a primary alkylation system adapted to receive the preliminary output stream and contact the preliminary output stream and the alkylating agent with a primary alkylation catalyst disposed therein so as to form a primary output stream.

One or more embodiments include the system of the preceding paragraph, wherein the system is adapted to regenerate the preliminary alkylation catalyst in-situ in one of the preliminary alkylation reactors simultaneous with contact of the preliminary alkylation catalyst with the aromatic compound and the alkylating agent in the other preliminary alkylation reactor.

One or more embodiments include the system of any preceding paragraph, wherein the preliminary output stream includes less than about 100 ppb of alkylation catalyst poisons.

One or more embodiments include the system of any preceding paragraph, wherein the preliminary alkylation catalyst includes a zeolite beta catalyst.

One or more embodiments include the system of any preceding paragraph, wherein the preliminary alkylation catalyst includes a cerium promoted beta zeolite catalyst.

One or more embodiments include the system of any preceding paragraph, wherein a $SiO_2/Al_2O_3$ ratio of the preliminary alkylation catalyst includes about 100:1 or less.

One or more embodiments include the system of any preceding paragraph, wherein the preliminary alkylation system, the primary alkylation system or combinations thereof are adapted to operate under liquid phase conditions.

One or more embodiments include an alkylation process. The alkylation process generally includes providing an aromatic compound and an alkylating agent; contacting the aromatic compound and the alkylating agent with a preliminary alkylation catalyst within a preliminary alkylation system so as to alkylate the aromatic compound and form a preliminary output stream, wherein the preliminary alkylation system includes a first preliminary alkylation reactor and a second preliminary alkylation reactor connected in parallel to the first preliminary alkylation reactor; passing the preliminary output stream to a primary alkylation system; and contacting the preliminary output stream and the alkylating agent with a primary alkylation catalyst disposed therein so as to form a primary output stream.

One or more embodiments include the process of the preceding paragraph, wherein the preliminary alkylation catalyst includes a cerium promoted zeolite beta.

One or more embodiments include the process of any preceding paragraph, wherein flow of the aromatic compound and the alkylating agent is terminated to one of the preliminary alkylation reactors for maintenance thereof, while flow continues in the other preliminary alkylation reactor.

One or more embodiments include the process of any preceding paragraph, wherein the maintenance includes catalyst regeneration.

One or more embodiments include the process of any preceding paragraph, wherein the preliminary alkylation catalyst has a catalyst life of at least 3 weeks prior to regeneration.

One or more embodiments include the process of any preceding paragraph, wherein the preliminary alkylation output including less than 100 ppb alkylation catalyst poisons.

One or more embodiments include the process of any preceding paragraph, wherein the process is absent a guard bed prior to the preliminary alkylation system.

One or more embodiments include the process of any preceding paragraph, wherein the regeneration occurs within the preliminary alkylation system.

DETAILED DESCRIPTION

Introduction and Definitions

Figure 1:
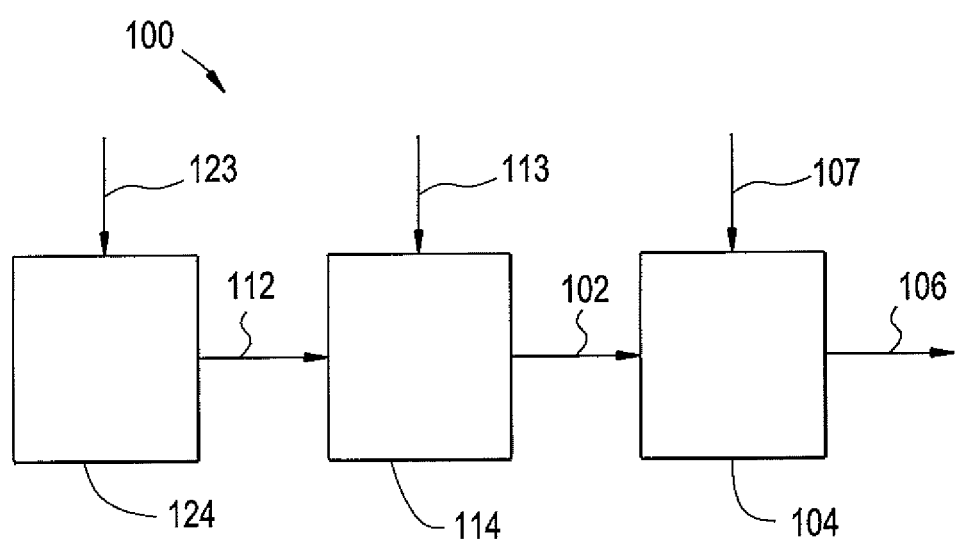
FIG. 1 illustrates a flow diagram of a prior art alkylation system.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

The term "activity" refers to the weight of product produced per weight of the catalyst used in a process per hour of reaction at a standard set of conditions (e.g., grams product/gram catalyst/hr).

The term "alkylation" refers to the addition of an alkyl group to another molecule.

The term "deactivated catalyst" refers to a catalyst that has lost enough catalyst activity to no longer be efficient in a specified process. Such efficiency is determined by individual process parameters. Further, the time from introduction of the catalyst to a system to the point that the catalyst is a deactivated catalyst is generally referred to as the catalyst life.

The term "processing" is not limiting and includes agitating, mixing, milling, blending and combinations thereof, all of which are used interchangeably herein. Unless otherwise specified, the processing may occur in one or more vessels, such vessels being known to one skilled in the art.

The term "recycle" refers to returning an output of a system as input to either that same system or another system within a process. The output may be recycled to the system in any manner known to one skilled in the art, for example, by combining the output with an input stream or by directly feeding the output into the system. In addition, multiple input/recycle streams may be fed to a system in any manner known to one skilled in the art.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

The term "maintenance" may include catalyst regeneration, catalyst replacement, system cleaning, equipment repair, equipment cleaning, and/or any other maintenance typical for alkylation systems.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process. The term "zeolite" refers to a molecular sieve containing a silicate lattice, often in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

The term "fresh benzene source" refers to a source including at least about 95 wt. % benzene, at least about 98 wt. % benzene or at least about 99 wt. % benzene, for example.

FIG. 1 illustrates a simplified flow diagram of a prior art alkylation process 100. Although not shown herein, any process stream flow may be modified based on unit optimization so long as the modification complies with the spirit of the invention, as defined by the claims. For example, at least a portion of any overhead fraction may be recycled as input to any other system within the process and/or any process stream may be split into multiple process stream inputs, for example. Also, additional process equipment, such as heat exchangers, may be employed throughout the processes described herein and such placement is generally known to one skilled in the art. Further, while described below in terms of primary components, the streams indicated below may include any additional components as known to one skilled in the art.

The process 100 generally includes supplying an input stream 102 to an alkylation system 104. The alkylation system 104 is generally adapted to contact the input stream 102 with an alkylation catalyst to form an alkylation output stream 106. In addition to the input stream 102, an additional input, such as an alkylating agent, may be supplied to the alkylation system 104 via line 103 (while illustrated as a separate input to the alkylation system 104, it is contemplated that the line 103 may be supplied to the input stream 102, for example).

The input stream 102 generally includes a first aromatic compound. The first aromatic compound may include substituted or unsubstituted aromatic compounds. If present, the substituents on the first aromatic compounds may be independently selected from alkyl, aryl, alkaryl, alkoxy, aryloxy, cycloalkyl, halide and/or other groups that do not interfere with the alkylation reaction, for example. Examples of substituted first aromatic compounds generally include toluene, xylene, isopropylbenzene, normal propylbenzene, alpha-methylnaphthalene, ethylbenzene, mesitylene, durene, cymene, butylbenzene, pseudocumene, o-diethylbenzene, m-diethylbenzene, p-diethyl benzene, isoamylbenzene, isohexylbenzene, pentaethylbenzene, pentamethyl benzene, 1,2,3,4-tetraethyl benzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, 4-ethyl-m-xylene, dimethylnaphthalenes, ethylnaphthalene, 2,3-dimethylanthracene, 9-ethylanthracene, 2-methylanthracene, o-methylanthracene, 9,10-dimethylphenanthrene and 3-methyl-phenanthrene. Further examples of first aromatic compounds include hexylbenzene, nonylbenzene, dodecylbenzene, pentadecylbenzene, hexyltoluene, nonyltoluene, dodecyltoluene and pentadecytoluene. Often, the first aromatic compound includes one or more hydrocarbons, such as benzene, naphthalene, anthracene, naphthacene, perylene, coronene and phenanthrene, for example. In many specific processes, the first aromatic compound includes benzene. The benzene may be supplied from a variety of sources, such as a fresh benzene source and/or a variety of recycle sources, for example. As used herein, the term "fresh benzene source" refers to a source including at least about 95 wt. % benzene, at least about 98 wt. % benzene or at least about 99 wt. % benzene, for example.

The alkylating agent may include olefins (e.g., ethylene, propylene, butene and pentene), alcohols (e.g., methanol, ethanol, propanol, butanol and pentanol), aldehydes (e.g., formaldehyde, acetaldehyde, propionaldehyde, butyraldehyde and n-valeraldehyde) and/or alkyl halides (e.g., methyl chloride, ethyl chloride, propyl chloride, butyl chloride and pentyl chloride), for example. Often, the alkylating agent includes a mixture of light olefins, such as mixtures of ethylene, propylene, butene and/or pentenes, for example. In many specific processes, such as those utilizing benzene as the first aromatic compound, the alkylating agent includes ethylene.

The alkylation system 104 generally includes one or more reaction vessels. The reaction vessels may include continuous flow reactors (e.g., fixed-bed, slurry bed or fluidized bed,) for example. Often, the alkylation system 104 includes a plurality of multi-stage reaction vessels. For example, the plurality of multi-stage reaction vessels may include a plurality of operably connected catalyst beds, such beds containing an alkylation catalyst. The number of catalyst beds is generally determined by individual process parameters, but may include from 1 to 100 catalyst beds, or from 2 to 20 catalyst beds or from 3 to 10 catalyst beds, for example.

Such reaction vessels may be liquid phase, vapor phase, supercritical phase or mixed phase reactors operated at reactor temperatures and pressures sufficient to maintain the alkylation reaction in the corresponding phase, i.e., the phase of the aromatic compound, for example. Such temperatures and pressures are generally determined by individual process parameters. Often, the plurality of stages within a reaction vessel may be operated with the same or different catalyst and at the same or different temperatures and space velocities. Such temperatures and pressures are generally determined by individual process parameters. However, liquid phase reactions may occur at temperatures of from about 160° C. to about 270° C. and pressures of at least about 400 psig, for example. Vapor phase reactions may occur at temperatures of from about 350° C. to about 500° C. and pressures of from about 200 psig to about 355 psig, for example.

The alkylation catalyst may include a molecular sieve catalyst. Such molecular sieve catalyst may include zeolite beta, zeolite Y, 25M-5, zeolite MCM-22, zeolite MCM-36, zeolite MCM-49 or zeolite MCM-56, for example. In one or more processes, the catalyst is a zeolite beta having a silica to alumina molar ratio (expressed as $SiO_2/Al_2O_3$) of from about 10 to about 200 or about 20 to about 50, for example. The zeolite beta may have a low sodium content, e.g., less than about 0.2 wt. % expressed as $Na_2O$, or less than about 0.02 wt. %, for example. The sodium content may be reduced by any method known to one skilled in the art, such as through ion exchange, for example. (See, U.S. Pat. No. 3,308,069 and U.S. Pat. No. 4,642,226 (formation of zeolite beta), U.S. Pat. No. 4,185,040 (formation of zeolite Y), U.S. Pat. No. 4,992,606 (formation of MCM-22), U.S. Pat. No. 5,258,565 (formation of MCM-36), WO 94/29245 (formation of MCM-49) and U.S. Pat. No. 5,453,554 (formation, of MGM-56), which are incorporated by reference herein.)

The alkylation catalyst may optionally be bound into any suitable shape including extrusion with any binder material. The support material may include alumina, silica, aluminosilicate, titanium, aluminum phosphate and/or clay, for example.

The alkylation output 106 generally includes a second aromatic compound formed from the reaction of the first aromatic compound and the alkylating agent in the presence of the alkylation catalyst, for example. The specific composition of the second aromatic compound depends upon the specific first aromatic compound and the alkylating agent. For example, when the first aromatic compound includes benzene and the first alkylating agent includes ethylene, the second aromatic compound includes ethylbenzene. In such processes, the molar ratio of benzene to ethylene entering the alkylation system 104 at each catalyst bed may be from about 1:1 to about 30:1, or from about 1:1 to about 20:1 or from about 2:1 to about 15:1 and the space velocity may be from about 2 to about 60, for example.

Unfortunately, the first alkylation catalyst bed of the alkylation catalyst system generally experience more rapid deactivation than subsequent catalyst beds upon exposure to the aromatic substrate. The life of the catalyst generally depends on process conditions and catalyst type. However, when regeneration of any catalyst within the system is desired, the regeneration procedure generally includes processing the deactivated catalyst at high temperatures, although the regeneration may include any regeneration procedure known to one skilled in the art.

Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the catalyst to a temperature or a series of temperatures, such as a regeneration temperature of from about 50° C. to about 400° C. above the purging or reaction temperature, for example.

Catalyst deactivation may be accelerated due to the presence of compounds, sometimes referred to as poisons, in either the first aromatic compound or the alkylating agent. The compounds may include compounds, such as amines or alcohols, for example. In order to reduce the deactivation of the alkylation catalyst due to catalyst poisons, it is desirable to reduce the level of such compounds in the input stream 102 to less than about 100 ppb or less than about 30 ppb, for example.

Therefore, alkylation processes 100 often include a preliminary alkylation system 114 adapted to receive the first aromatic compound via line 112 and an alkylating agent via line 113 and contact such with an alkylation catalyst to reduce the level of poisons present in the first alkylating agent entering the alkylation system 114 via line 102. The level of poisons may be reduced to undetectable levels or by at least 10%, or at least 20% or at least 30% or at least 40% or at least 50%, for example.

The preliminary alkylation system 114 may be maintained at ambient or up to alkylation conditions. For example, the preliminary alkylation system 114 may be operated under liquid phase or vapor phase conditions. For example, the preliminary alkylation system 114 may be operated at a temperature of from about 20° C. to about 270° C. and a pressure of from about 97 psi to about 1200 psi.

The preliminary alkylation system 114 generally includes a preliminary catalyst disposed therein. The preliminary catalyst may include any of those alkylation catalysts described previously herein. Often the preliminary catalyst varies from that disposed within the alkylation system 104, but it is contemplated that such catalysts may be the same type of alkylation catalyst.

As a result of the level of poisons present in the preliminary alkylation input 112, the preliminary catalyst may be deactivated rapidly, requiring frequent regeneration and/or replacement. For example, the preliminary catalyst may experience deactivation more rapidly than the alkylation catalyst (e.g., twice as often or 1.5 times as often).

Prior art systems often address such rapid deactivation of the preliminary catalyst through use of one or more guard beds 124. The guard beds 124 may include a material adapted to reduce the amount of poisons present in the first aromatic compound entering the guard bed 124 via line 123.

However, embodiments of the invention are capable of reducing preliminary catalyst deactivation and/or system shutdowns due to preliminary catalyst deactivation through a number of features. First, one or more embodiments of the invention utilize a cerium promoted catalyst.

In one embodiment, the cerium promoted zeolite catalyst is a cerium promoted zeolite beta catalyst. The cerium promoted zeolite beta (e.g., cerium beta) catalyst may be formed from any zeolite catalyst known to one skilled in the art. For example, the cerium beta catalyst may include zeolite beta modified by the inclusion of cerium. The zeolite beta may have a silica to alumina molar ratio (expressed as $SiO_2/Al_2O_3$) of from about 10 to about 200 or about 20 to about 50, for example. In one embodiment, the zeolite beta may have a low sodium content, e.g., less than about 0.2 wt. % expressed as $Na_2O$, or less than about 0.02 wt. %, for example. The sodium content may be reduced by any method known to one skilled in the art, such as through ion exchange, for example. The formation of zeolite beta is further described in U.S. Pat. No. 3,308,069 and U.S. Pat. No. 4,642,226, which are incorporated by reference herein.

In another embodiment, it is contemplated that a cerium promoted zeolite Y catalyst may be used. It is further contemplated that the zeolite Y catalyst may be modified with cerium in the same manner as the modification of zeolite beta. The formation of Zeolite Y is described in U.S. Pat. No. 4,185,040, which is incorporated by reference herein.

Unexpectedly, it has been found that the cerium promoted zeolite catalyst can be regenerated to a level higher than that of previous zeolite catalysts utilized in the preliminary alkylation system 103. Such unexpected regeneration provides for increased catalyst activity and/or longer run times between regeneration and/or replacement of the catalyst.

In one embodiment, the zeolite catalyst is modified with a rare earth metal ion, such as lanthanum, cerium, neodymium or praseodymium, for example. As previously discussed, it has been discovered that cerium based zeolite catalyst demonstrate an unexpected improvement in activity and selectivity over lanthanum based zeolite catalyst systems. However, it is contemplated that the acidity of the rare earth metal ion based zeolite catalyst systems may be modified to enhance the activity and/or selectivity thereof. Such modification of the acidity may be accomplished through the processes described in J. Catal. 205, 58-66 (2002), which is incorporated by reference herein.

Figure 2:
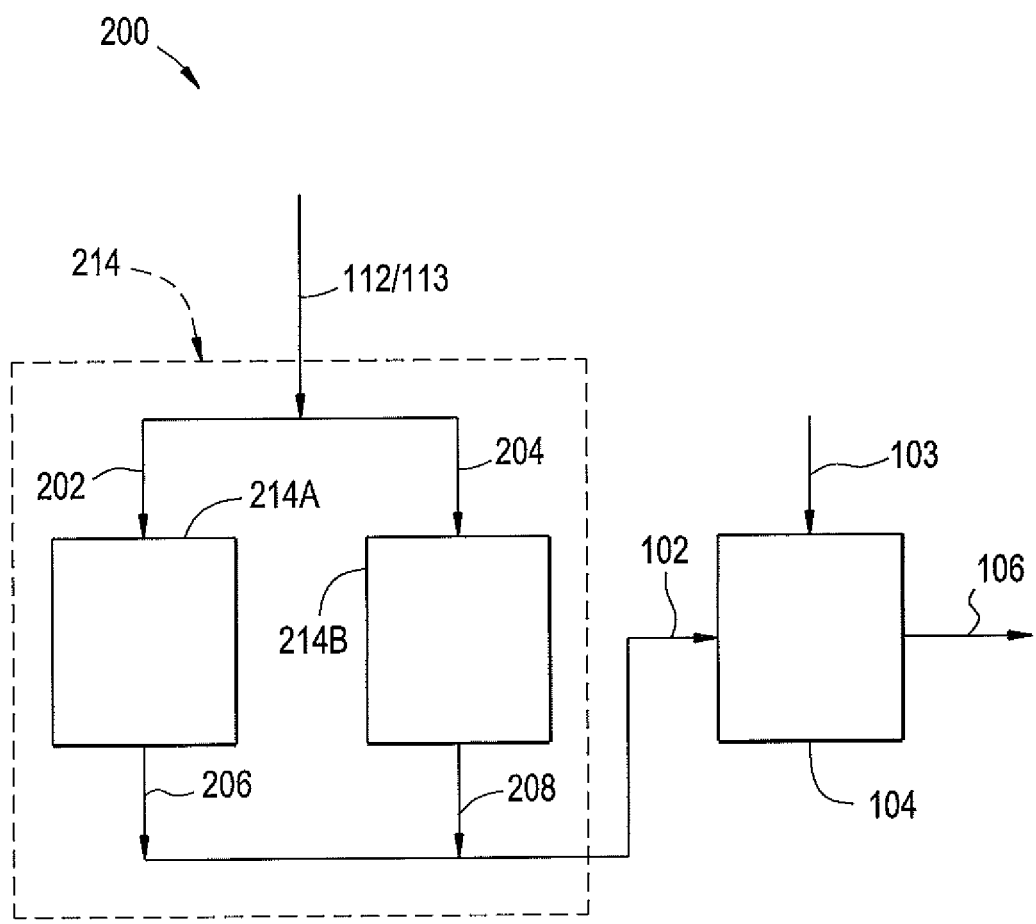
FIG. 2 illustrates a flow diagram of an embodiment of an inventive alkylation system.

Second, embodiments of the invention utilize a process 200, such as that illustrated in FIG. 2. The process 200 generally includes an alkylation reactor 104, such as that described previously herein.

The process 200 further includes a preliminary alkylation system 214. The preliminary alkylation system 214 includes those components discussed previously herein, such as catalyst, process conditions and flow configuration into and out of such. However, in contrast to the preliminary alkylation system 114, the preliminary alkylation system 214 generally utilizes a swing reactor configuration. The swing reactor configuration includes a first preliminary alkylation reactor 214A and a second preliminary alkylation reactor 214B. The first aromatic compound may be fed to the first preliminary alkylation reactor 214A, the second preliminary alkylation reactor 214B or combinations thereof.

In one or more embodiments, the individual reactors of the preliminary alkylation system 214 operate in parallel. For example, one or both preliminary alkylation reactors 214A and 214B, which may be the same type of reaction vessel, or, in certain embodiments, may be different types of reaction vessels, may be placed on-stream at the same time so that both reactors are in service simultaneously. Alternatively, the first preliminary alkylation reactor 214A may be on-stream while the second preliminary alkylation reactor 214B undergoes maintenance, such as regeneration or replacement of the preliminary alkylation catalyst disposed therein. Alternatively, the second preliminary alkylation reactor 214B may be on-stream while the first preliminary alkylation reactor 214A undergoes maintenance. In one embodiment, the preliminary alkylation system 214 may be configured so that the input stream 112/13 may be split equally in stream 202 and 204 so as to supply approximately the same amounts of aromatic compound to each preliminary alkylation reactor 214A and 214B, resulting in outputs 206 and 208. However, such flow rates may be determined for each individual system, and valves or other flow-control devices may be used to control the flow of input stream 112/113 to the preliminary alkylation reactors 214A and 214B.

In parallel operation, the first and second preliminary alkylation reactors 214A and 214B may operate at relatively lower space velocities for prolonged periods of time when both reactors 214A and 214B are on-stream, with periodic relatively short periods of operation at enhanced, relatively higher space velocities when one reactor, such as reactor 214A may be taken off-stream while reactor 214B remains on-stream. By way of example, during normal operation of the preliminary alkylation system 214, and with both reactors 214A and 214B on-stream, the input stream 112/113 may be supplied to each reactor (e.g., via stream 202 and 204 for reactors 214A and 214B, respectively) to provide a reduced space velocity. When one of the reactors, such as reactor 214A, may be taken off-stream and the feed rate of input stream 112/113 continues unabated, the space velocity for the remaining reactor, such as reactor 214B, may approximately double. The space velocity may be from about 2 to about 100 for the preliminary reactors 214A and 214B, for example. However, it is to be noted that the space velocity depends upon the amount of catalyst poisons in the input stream 112/113.

The preliminary alkylation system 214 may be maintained at ambient or up to preliminary alkylation conditions, for example. For example, the preliminary alkylation system 214 may operate under liquid phase conditions. For further example, the preliminary alkylation system 214 may operate at a temperature of from about 20° to about 270° C. and a pressure of from about 97 psi to about 1,200 psi.

The fluidly-parallel orientation of preliminary alkylation reactors 214A and 214B allows for alternating regeneration or replacement of the preliminary alkylation catalyst disposed with either preliminary reactor while the other reactor is on-stream. Thus, the preliminary alkylation system 214 need not go completely off-stream in order to regenerate or replace the preliminary alkylation catalyst, thereby keeping the primary alkylation system 214, and the alkylation system 200, on-stream.

It is further contemplated that the embodiments described herein may be capable of adequate operation even in the absence of guard beds, such as guard beds 124 described in FIG. 1. For example, it has been observed that preliminary alkylation systems utilizing cerium promoted alkylation catalysts are capable of extended operation, such as up to 3 months, without regeneration. Accordingly, it is expected that embodiments of the present invention utilizing cerium promoted alkylation catalysts in the preliminary alkylation system 214 may be capable of individual operation of weeks, such as up to 3 weeks, without regeneration, even in the absence of guard beds.

Furthermore, embodiments of the invention are capable of regenerating the preliminary catalysts in-situ, thereby removing additional system and processing equipment and energy requirements.

While the foregoing is directed to embodiments of the present invention, other and further embodiments of the invention may be devised without departing from the basic scope thereof and the scope thereof is determined by the claims that follow and their legal equivalents.

What is claimed is:

1. An alkylation system comprising:
   a preliminary alkylation system comprising a first preliminary alkylation reactor and a second preliminary alkylation reactor, wherein the second preliminary alkylation reactor is connected in parallel to the first preliminary alkylation reactor, wherein each preliminary alkylation reactor contains a preliminary alkylation catalyst therein, and wherein each preliminary alkylation catalyst in the preliminary alkylation system has a silica to alumina molar ratio ranging from 10 to 200;
   wherein the preliminary alkylation system is adapted to contact an aromatic compound and an alkylating agent with the preliminary alkylation catalyst so as to alkylate the aromatic compound and form a preliminary output stream, wherein the preliminary alkylation system is adapted to operate under liquid phase conditions at a temperature of from about 160° C. to about 270° C.; and
   a primary alkylation system adapted to receive the preliminary output stream and contact the preliminary output stream and an alkylating agent with a primary alkylation catalyst disposed therein so as to form a primary output stream, wherein the preliminary alkylation system is located upstream of the primary alkylation system.

2. The system of claim 1, wherein the system is adapted to regenerate the preliminary alkylation catalyst in-situ in one of the preliminary alkylation reactors simultaneous with contact of the preliminary alkylation catalyst with the aromatic compound and the alkylating agent in the other preliminary alkylation reactor.

3. The system of claim 1, wherein the preliminary alkylation system is adapted to reduce a level of poisons present in the alkylating agent to less than about 100 ppb of alkylation catalyst poisons.

4. The system of claim 1, wherein the preliminary alkylation catalyst comprises a zeolite beta catalyst.

5. The system of claim 1, wherein the preliminary alkylation catalyst comprises a cerium promoted beta zeolite catalyst.

6. The system of claim 1, wherein the silica to alumina molar ratio of each preliminary alkylation catalyst is less than 100.

7. The system of claim 1, wherein the primary alkylation system is adapted to operate under liquid phase conditions.

8. The system of claim 1, wherein the system lacks a guard bed prior to the preliminary alkylation system.

9. The system of claim 1, wherein the preliminary alkylation system is adapted to operate at pressure of from about 97 psi to about 1200 psi.

10. The system of claim 1, wherein the preliminary alkylation catalyst comprises a cerium promoted zeolite Y catalyst.

11. The system of claim 1, wherein the primary alkylation catalyst has a silica to alumina molar ratio ranging from 10 to 200.

12. An alkylation system comprising:
    a preliminary alkylation system comprising a first preliminary alkylation reactor and a second preliminary alkylation reactor, wherein the second preliminary alkylation reactor is connected in parallel to the first preliminary alkylation reactor, wherein each preliminary alkylation reactor contains a preliminary alkylation catalyst therein, and wherein each preliminary alkylation catalyst in the preliminary alkylation system has a silica to alumina molar ratio ranging from 10 to 200;
    wherein the preliminary alkylation system is adapted to contact an aromatic compound and an alkylating agent with the preliminary alkylation catalyst so as to alkylate the aromatic compound and form a preliminary output stream, wherein the preliminary alkylation system is adapted to operate at a temperature of from about 160° C. to about 270° C. and a pressure of from about 97 psi to about 1200 psi; and
    a primary alkylation system adapted to receive the preliminary output stream and contact the preliminary output stream and an alkylating agent with a primary alkylation catalyst disposed therein so as to form a primary output stream, wherein the preliminary alkylation system is located upstream of the primary alkylation system.

13. The system of claim 12, wherein the primary alkylation catalyst has a silica to alumina molar ratio ranging from 10 to 200.

14. An alkylation system comprising:
    a preliminary alkylation system comprising a first preliminary alkylation reactor and a second preliminary alkylation reactor, wherein the second preliminary alkylation reactor is connected in parallel to the first preliminary alkylation reactor;
    wherein each preliminary alkylation reactor contains a cerium promoted beta zeolite catalyst having a silica to alumina molar ratio of from 10 to 200 therein or a cerium promoted zeolite Y catalyst having a silica to alumina molar ratio of from 10 to 200 therein;
    wherein the preliminary alkylation system is adapted to contact an aromatic compound and an alkylating agent with the preliminary alkylation catalyst so as to alkylate the aromatic compound and form a preliminary output stream, wherein the preliminary alkylation system is adapted to operate under liquid phase conditions at a temperature of from about 160° C. to about 270° C. and a pressure of from about 97 psi to about 1200 psi, wherein the preliminary alkylation system is adapted to reduce a level of poisons present in the alkylating agent to less than about 100 ppb of alkylation catalyst poisons;
    a primary alkylation system adapted to receive the preliminary output stream and contact the preliminary output stream and an alkylating agent with a primary alkylation catalyst having a silica to alumina molar ratio ranging from 10 to 200 disposed therein so as to form a primary output stream, wherein the primary alkylation system is adapted to operate under liquid phase conditions, wherein the preliminary alkylation system is located upstream of the primary alkylation system;
    wherein the system lacks a guard bed prior to the preliminary alkylation system; and
    wherein the system is adapted to regenerate the preliminary alkylation catalyst in-situ in one of the preliminary alkylation reactors simultaneous with contact of the preliminary alkylation catalyst with the aromatic compound and the alkylating agent in the other preliminary alkylation reactor.

* * * * *